US010092388B2

(12) United States Patent
Toomey

(10) Patent No.: US 10,092,388 B2
(45) Date of Patent: Oct. 9, 2018

(54) ANTI-LEAKAGE PROSTHESIS

(71) Applicant: Cook Medical Technologies LLC, Bloomington, IN (US)

(72) Inventor: Ciarán Toomey, Rathcormac (IE)

(73) Assignee: Cook Medical Technologies LLC, Bloomington, IN (US)

(*) Notice: Subject to any disclaimer, the term of this patent is extended or adjusted under 35 U.S.C. 154(b) by 184 days.

(21) Appl. No.: 14/939,696

(22) Filed: Nov. 12, 2015

(65) Prior Publication Data

US 2016/0058545 A1 Mar. 3, 2016

Related U.S. Application Data

(62) Division of application No. 13/709,234, filed on Dec. 10, 2012, now abandoned.

(Continued)

(51) Int. Cl.
*A61F 2/82* (2013.01)
*A61F 2/04* (2013.01)
(Continued)

(52) U.S. Cl.
CPC ............ *A61F 2/04* (2013.01); *A61B 17/1114* (2013.01); *A61B 17/22* (2013.01); *A61B 17/221* (2013.01);
(Continued)

(58) Field of Classification Search
CPC .......... A61F 2002/007; A61F 2002/041; A61F 2002/045; A61F 2/07
See application file for complete search history.

(56) References Cited

U.S. PATENT DOCUMENTS 5,476,434 A 12/1995 Kalb et al.
2003/0236567 A1 12/2003 Elliot
(Continued)

FOREIGN PATENT DOCUMENTS

WO WO 2011/118081 A1 9/2011
WO WO 2013/087096 A1 6/2013

OTHER PUBLICATIONS

Giovannini, Marc et al.; "EUS-Guided Biliary Drainage"; Review Article, Gastroenterology Research and Practice, vol. 2012, Article ID 348719, 5 pages; Hindawi Publishing Corporation; doi: 10.1155/2012/348719; 2012.
(Continued)

*Primary Examiner* — David Isabella
*Assistant Examiner* — Christine Nelson
(74) *Attorney, Agent, or Firm* — Brinks Gilson & Lione

(57) ABSTRACT

A prosthesis and a method for directing flow through a passageway formed between a first bodily lumen and a second bodily lumen are provided. The prosthesis includes a body having a proximal portion, a distal portion and a lumen extending therethrough. The prosthesis also includes a sleeve operably connected to the body at a connected portion. The sleeve has a proximal portion, a distal portion, and a sleeve lumen extending therethrough. At least a portion of the body is positioned within at least a portion of the sleeve lumen and the distal portion of the sleeve is free from connection to the distal portion of the body and extendable away from the body to contact a wall of the first bodily lumen. The sleeve is configured to allow fluid flow through the sleeve lumen from the first bodily lumen to the second bodily lumen.

18 Claims, 8 Drawing Sheets

Related U.S. Application Data

(60) Provisional application No. 61/576,152, filed on Dec. 15, 2011.

(51) Int. Cl.
| | | |
|---|---|---|
| *A61B 17/11* | (2006.01) | |
| *A61B 17/22* | (2006.01) | |
| *A61B 17/221* | (2006.01) | |
| *A61F 2/86* | (2013.01) | |
| *A61F 2/94* | (2013.01) | |
| *A61F 2/06* | (2013.01) | |
| *A61F 2/07* | (2013.01) | |
| *A61M 27/00* | (2006.01) | |

(52) U.S. Cl.
CPC .................. *A61F 2/07* (2013.01); *A61F 2/82* (2013.01); *A61F 2/86* (2013.01); *A61F 2/94* (2013.01); *A61B 2017/2215* (2013.01); *A61B 2017/22034* (2013.01); *A61B 2017/22044* (2013.01); *A61B 2217/005* (2013.01); *A61F 2/064* (2013.01); *A61F 2002/041* (2013.01); *A61F 2002/075* (2013.01); *A61F 2250/0039* (2013.01); *A61M 27/008* (2013.01)

(56) References Cited

U.S. PATENT DOCUMENTS

| | | |
|---|---|---|
| 2007/0055360 A1 | 3/2007 | Hanson et al. |
| 2007/0179599 A1 | 8/2007 | Brodbeck et al. |
| 2008/0262595 A1 | 10/2008 | Chu et al. |
| 2009/0143713 A1 | 6/2009 | Van Dam et al. |
| 2010/0191167 A1 | 7/2010 | Laufer |
| 2011/0054381 A1* | 3/2011 | Van Dam ............ A61B 17/1114 604/8 |
| 2012/0095545 A1 | 4/2012 | Yamagata |
| 2013/0131827 A1 | 5/2013 | Cassivi et al. |

OTHER PUBLICATIONS

Yamao, Kenji et al.; "EUS-Guided Biliary Drainage"; Gut and Liver, vol. 4, Suppl. 1; Sep. 2010; pp. S67-S75.

* cited by examiner

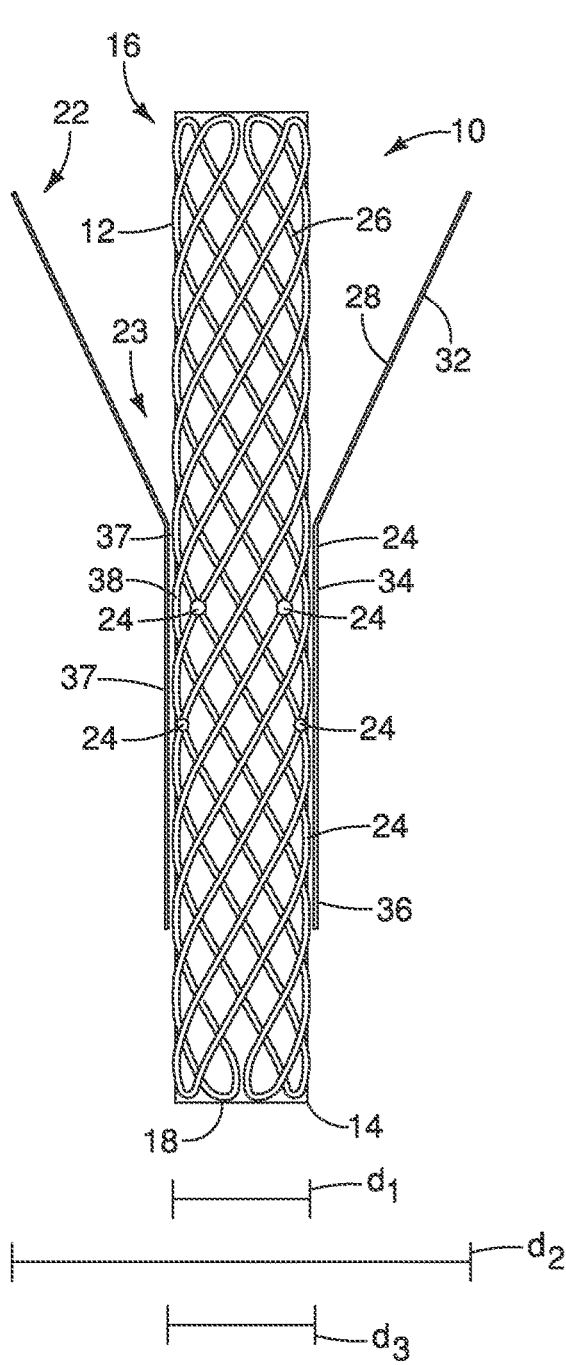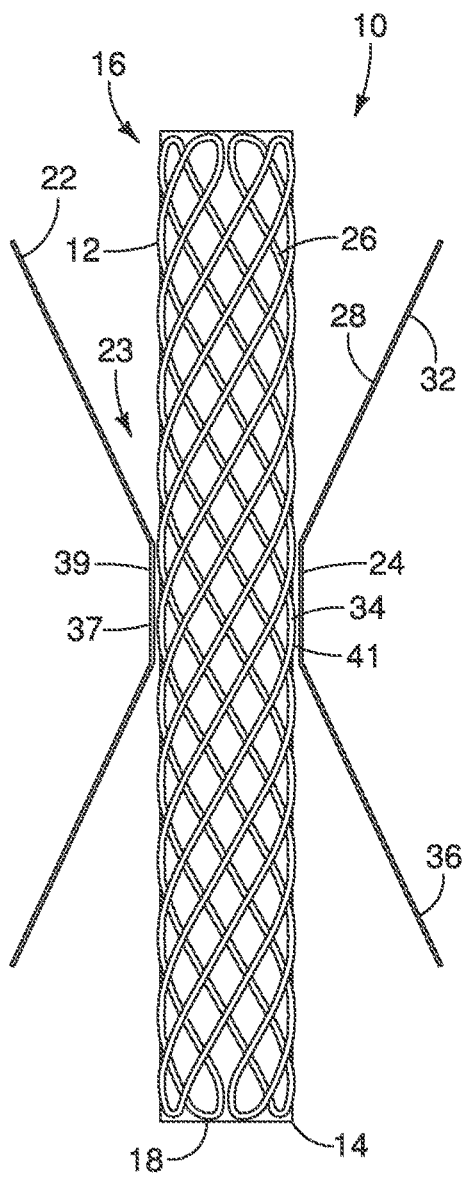
FIG. 1
FIG. 2

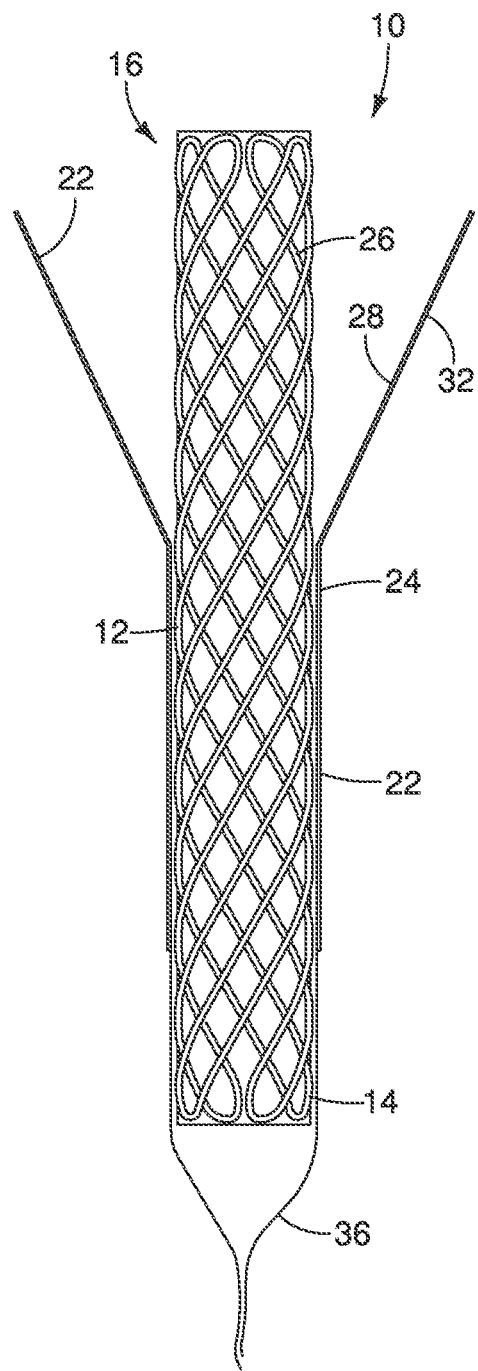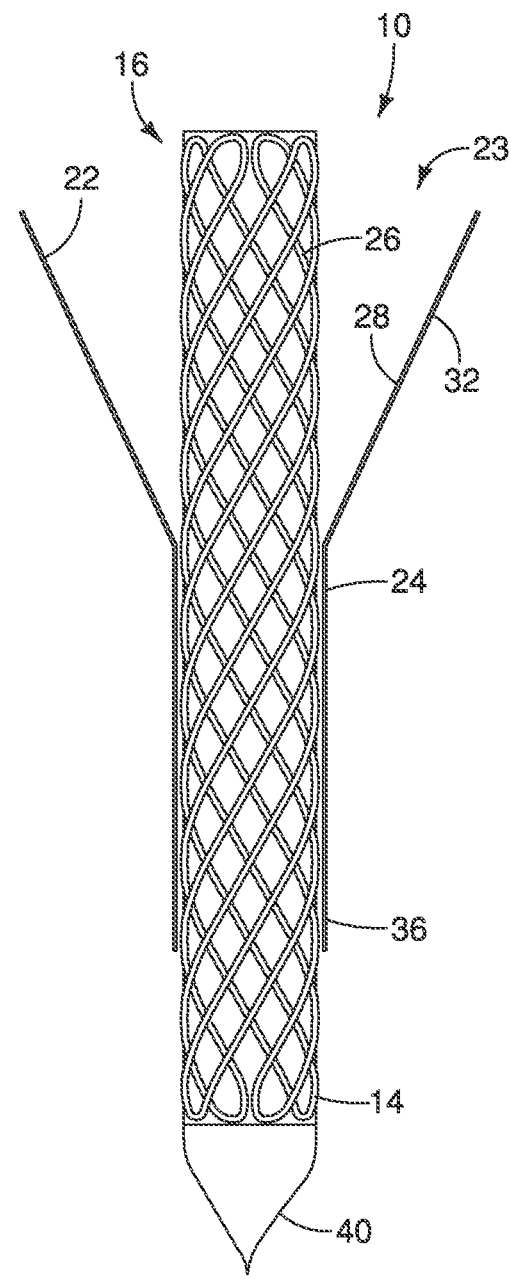
FIG. 3
FIG. 4

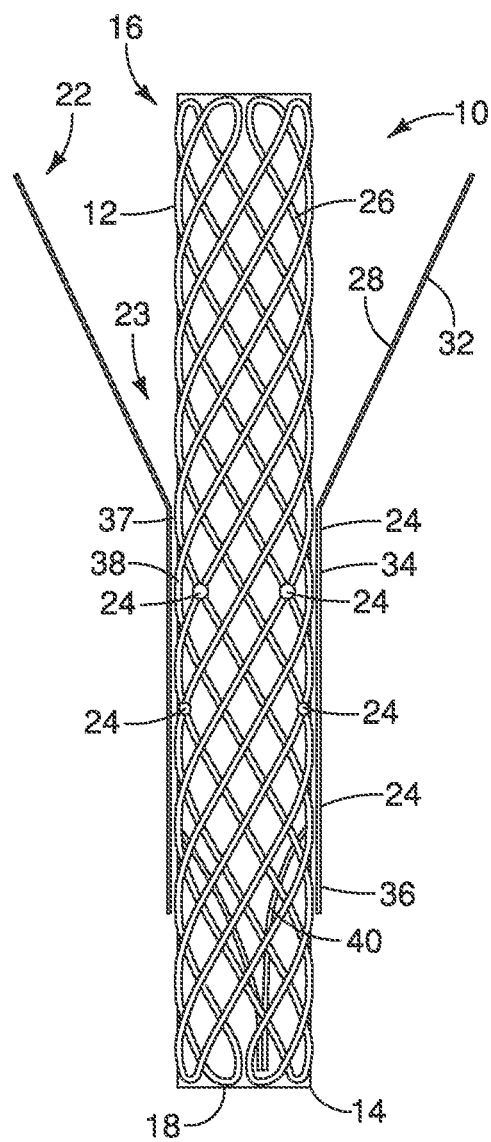
FIG. 5
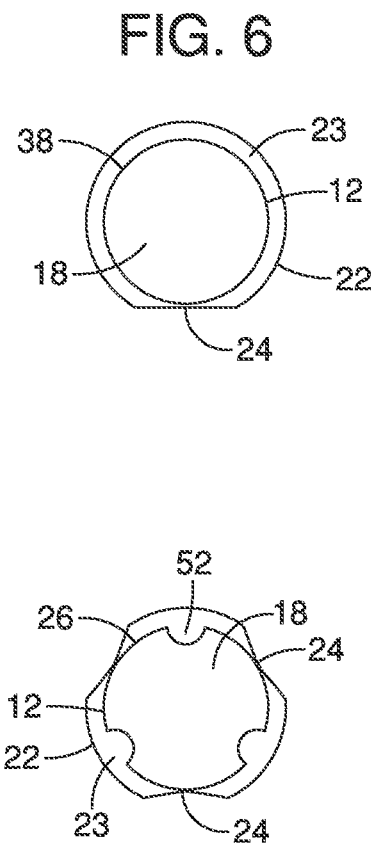
FIG. 6
FIG. 7

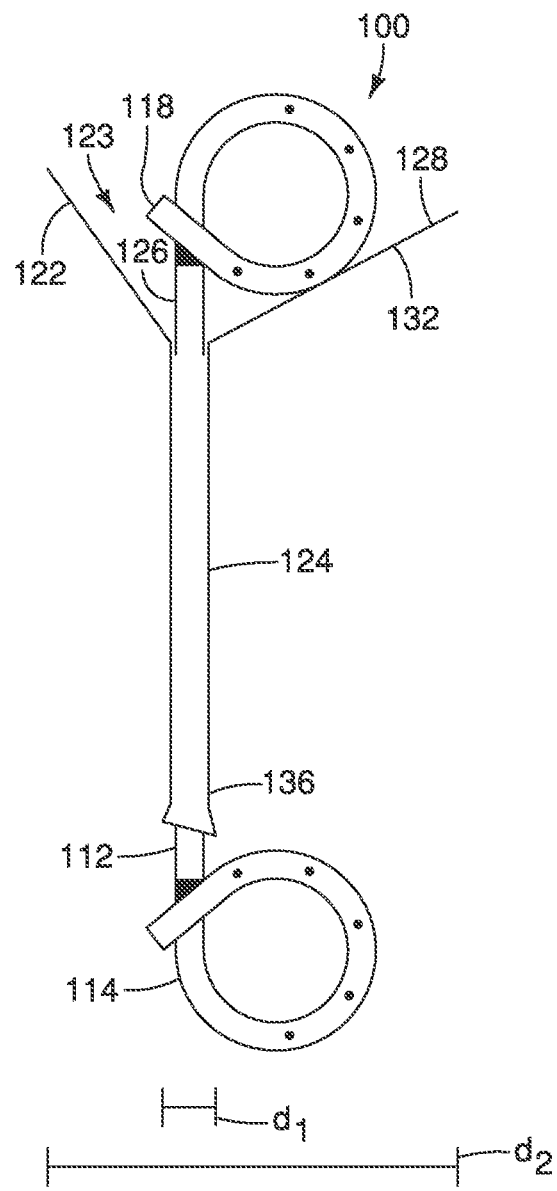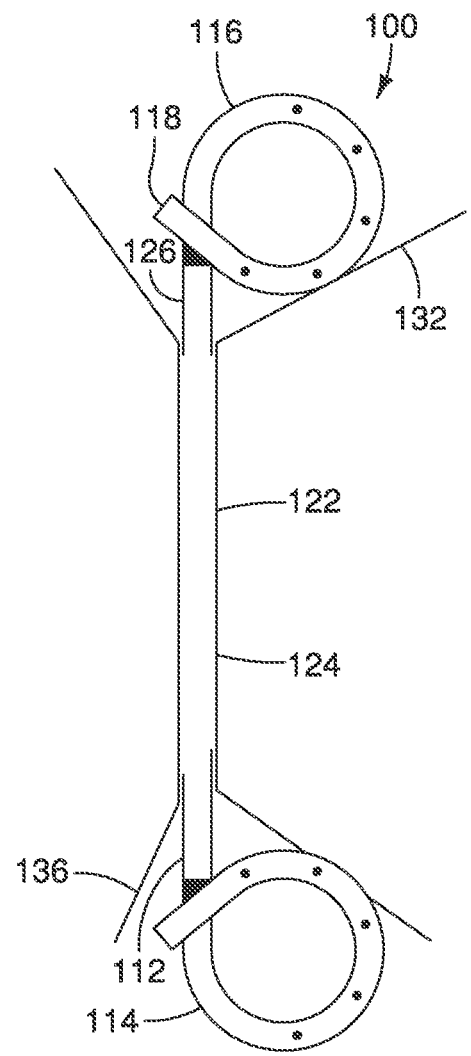
FIG. 8
FIG. 9

US 10,092,388 B2

ANTI-LEAKAGE PROSTHESIS

RELATED APPLICATIONS

This application is a divisional application of U.S. application Ser. No. 13/709,234, filed Dec. 10, 2012, which claims the benefit of U.S. Provisional Application No. 61/576,152, filed Dec. 15, 2011, which are incorporated by reference herein in their entirety.

FIELD OF THE INVENTION

The present invention relates to medical devices and methods and in particular to a prosthesis having a sleeve to prevent leakage after a medical procedure in the gastrointestinal tract.

BACKGROUND OF THE INVENTION

Endoscopic biliary stenting is typically used to treat bile duct obstruction. In some cases, ERCP treatment of the bile duct fails or is not a viable treatment and surgery or percutaneous biliary drainage may be needed. However, surgery and percutaneous biliary drainage have a relatively high complication rate. Recently, transgastric endoscopic ultrasonography (EUS) has been used to provide imaging of the left lobe of the liver, especially of dilated intrahepatic ducts in patients with biliary obstruction. Using EUS guidance, biliary drainage can be provided by hepaticogastrostomy or choledochoduodenstomy approaches for placing a stent for biliary decompression. Hepaticogastrostomy or choledochoduodenstomy approaches have been shown to have lower complication rates than surgery or percutaneous drainage.

One potential complication of the hepaticogastrostomy or choledochoduodenstomy approach to treating biliary obstruction is the potential for bile to leak into the peritoneum. Bile leaks into the peritoneum when the bile flows outside of the wall of a stent placed between the hepatic biliary system (including extrahepatic bile ducts and/or intrahepatic bile ducts) and the stomach or the duodenum.

What is needed in the art is a prosthesis and a method for biliary decompression that minimizes the potential for peritoneal biliary leakage.

BRIEF SUMMARY

Accordingly, it is an object of the present invention to provide a device and a method having features that resolve or improve on the above-described drawbacks.

A prosthesis and a method for directing flow through a passageway formed between a first bodily lumen and a second bodily lumen are provided. The prosthesis includes a body having a proximal portion, a distal portion and a lumen extending therethrough. The prosthesis also includes a sleeve operably connected to the body at a connected portion. The sleeve has a proximal portion, a distal portion, and a sleeve lumen extending therethrough. At least a portion of the body is positioned within at least a portion of the sleeve lumen and the distal portion of the sleeve is free from connection to the distal portion of the body and extendable away from the body to contact a wall of the first bodily lumen. The sleeve is configured to allow fluid flow through the sleeve lumen from the first bodily lumen to the second bodily lumen.

BRIEF DESCRIPTION OF THE DRAWINGS

FIG. 1 is a sectional view of a prosthetic device in accordance with an embodiment of the present invention;

FIG. 2 is a sectional view of a prosthetic device in accordance with an embodiment of the present invention;

FIG. 3 is a sectional view of a prosthetic device in accordance with an embodiment of the present invention;

FIG. 4 is a sectional view of a prosthetic device in accordance with an embodiment of the present invention;

FIG. 5 is a sectional view of a prosthetic device in accordance with an embodiment of the present invention;

FIG. 6 is a cross-sectional view of a prosthetic device in accordance with an embodiment of the present invention;

FIG. 7 is a cross-sectional view of a prosthetic device in accordance with an embodiment of the present invention;

FIG. 8 is a side view of a prosthetic device in accordance with an embodiment of the present invention;

FIG. 9 is a side view of a prosthetic device in accordance with an embodiment of the present invention;

DETAILED DESCRIPTION

Figures 10, 11:
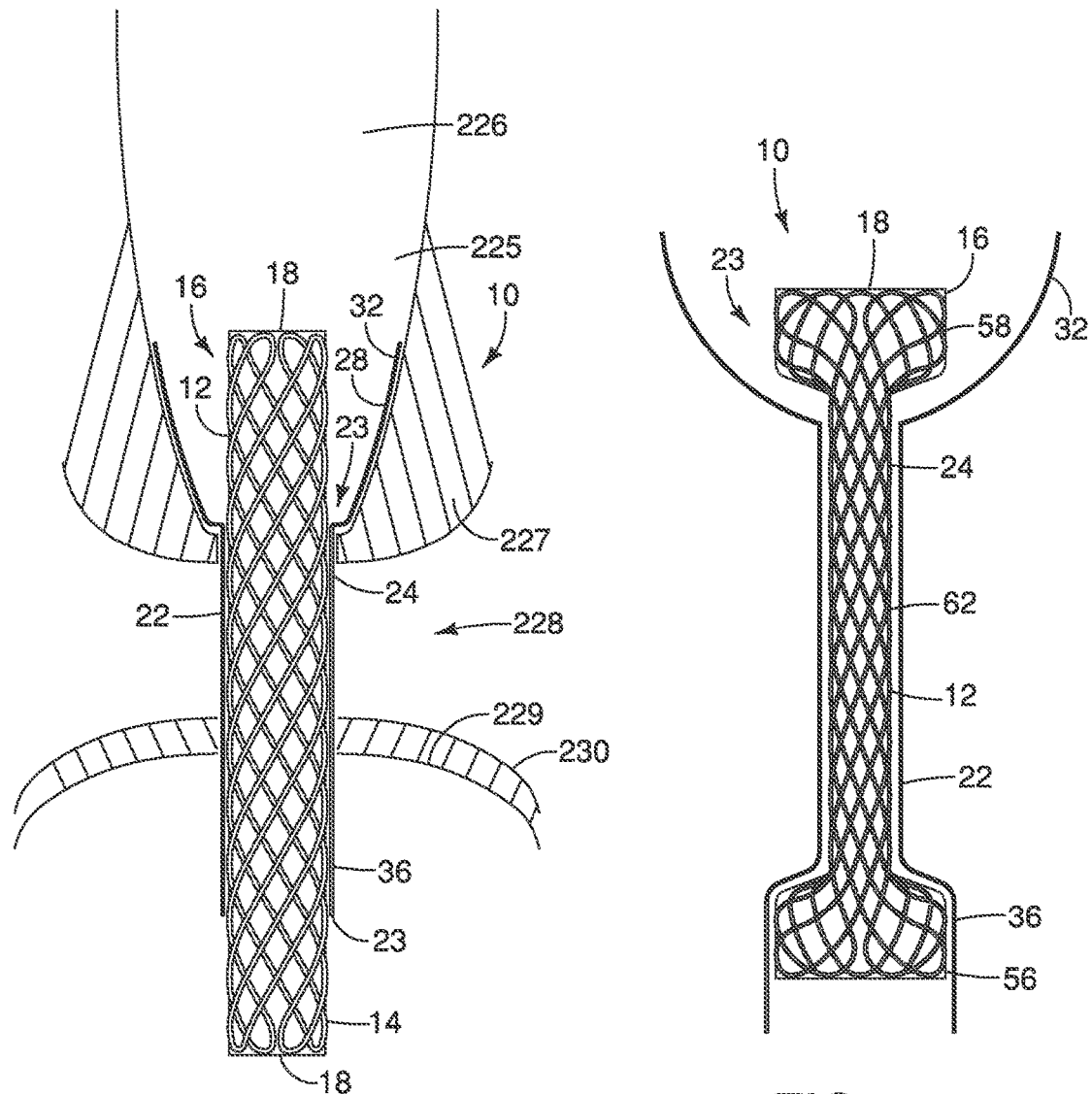
FIG. 10 is a sectional view of a prosthetic device in accordance with an embodiment of the present invention.
FIG. 11 illustrates an embodiment of a prosthetic device operably connecting the biliary tract and the gastrointestinal intestinal tract.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the prosthesis to a patient. Hence the term "distal" means the portion of the prosthesis that is farthest from the physician and the term "proximal" means the portion of the prosthesis that is nearest to the physician.

The present invention relates to medical devices, and in particular to a prosthesis for implantation in a body to form a conduit between two organs such as the bile duct and the stomach or the duodenum. As used herein, the term "implantable" refers to an ability of a medical device to be positioned at a location within a body, either temporarily, semi-permanently, or permanently. Permanent fixation of the device in a particular position is not required. Furthermore, the terms "implantation" and "implanted" refer to the positioning of a medical device at a location within a body.

FIG. 1 illustrates a prosthesis 10 in accordance with an embodiment of the present invention. The prosthesis 10 includes a body 12 having proximal portion 14, a distal portion 16 and a lumen 18 extending therethrough. In some embodiments, the body 12 may be an expandable stent, such as a self-expanding stent. The stent may be coated or non-coated. In some embodiments, the body 12 may be a non-expandable tubular stent.

The prosthesis 10 further includes a sleeve 22 having a connected portion 24 operably connecting the sleeve 22 to the body 12 at at least one position along the body 12. At least a portion of the body 12 extends through a portion of a sleeve lumen 23 so that the sleeve and body coextend, for example, across the peritoneum. The sleeve 22 is connected to the body 12 in such a way that fluid can pass through the sleeve lumen 23 between an outer surface 26 of the body 12 and an inner surface 28 of the sleeve 22. The connected portion 24 of the sleeve 22 is configured so that the connected portion 24 still allows fluid flow through the sleeve lumen 23 generally from a distal portion 32 of the sleeve 22 to a proximal portion 36 of the sleeve 22. In some embodiments, the connected portion 24 may be a single connection point. In some embodiments, the connected portion 24 may be a longitudinally extending connection so that a majority of a circumference 37 of the sleeve 22 is unconnected to the body 12. In yet other embodiments, the connected portion 24 may be a plurality of connections to the body 12, for example at points spaced apart around a circumference 38 of the body 12. By way of non-limiting example, the connected portions 24 may be spaced about by 60°, 90°, 120°, 180° and the like. Several rows of connected portions 24 may be used. Other connection configurations are also possible that connect the sleeve 22 to the body 12 and still allow fluid flow through the sleeve lumen 23 between the sleeve 22 and the body 12. As shown in FIG. 1, the connected portion 24 may be positioned away from the distal portion 16 of the body 12. In some embodiments, one or more connected portions 24 may be positioned at or near a mid portion 34 of the body 12. The connected portion 24 may be positioned so that the connected portion 24 is positioned within the bile duct or outside of the bile duct as described in more detail below.

As shown in FIGS. 1 and 2, the distal portion 32 of the sleeve 22 is unconnected to the body 12 of the prosthesis 10 and includes sufficient material to extend away from the body 12 as will be explained in more detail below. The sleeve 22 is formed of a liquid impermeable, thin, flexible polymeric material so that the liquid transported through the sleeve 22 exits at the proximal portion 36 of the sleeve 22 and not through a wall of the sleeve 22. The distal portion 32 of the sleeve 22 may be collapsed against the body 12 for delivery of the prosthesis 10 to the bodily lumen and then the distal portion 32 may be extended away from the body 12 when the prosthesis 10 is in positioned within the bodily lumen.

The proximal portion 36 of the sleeve 22 may be sized and shaped to fit close to the body 12 as shown in FIG. 1 or to include sufficient material to extend away from the body 12 as shown in FIG. 2. In some embodiments, the proximal portion 36 of the sleeve 22 may be connected to the body 12 by a connected portion 24. In other embodiments, the proximal portion 36 of the sleeve 22 may be unconnected to the body 12 and closely fit to the body 12 or extended away from the body 12. In some embodiments, the proximal portion 14 of the body 12 may extend proximal to the proximal portion 36 of the sleeve 22 as shown in FIG. 1. In some embodiments, the proximal portion 36 of the sleeve 22 may extend proximal to the proximal portion 14 of the body 12 as shown in FIG. 3 and described in more detail below. In some embodiments, a diameter $d_1$ of the proximal portion 36 of the sleeve 22 may be smaller than a diameter $d_2$ of the distal portion 32 of the sleeve 22 as shown in FIG. 1. In some embodiments, the diameter $d_1$ of the proximal portion 36 may be the same or greater than the diameter $d_2$ of the distal portion 36 of the sleeve 22. The diameter $d_2$ of the distal portion 36 of the sleeve 22 is greater than a diameter $d_3$ surrounding the mid portion 34 of the body 12. In some embodiments, a mid portion 37 of the sleeve 22 surrounding the mid portion 34 of the body 12 is sized so that a diameter 39 of the mid portion 37 of the sleeve 22 is slightly larger than a diameter 41 of the mid portion 34 of the body 12.

As shown in FIG. 3, the proximal portion 36 of the sleeve 22 may extend proximal to the proximal portion 14 of the body 12. As shown, the proximal portion 36 may close on itself in the absence of fluid flowing through the body 12 or the sleeve 22. In some embodiments, the proximal portion 36 may form a one-way valve that allows bile to flow into the duodenum or the stomach but prevents contents from the duodenum or the stomach from traveling through the lumen 18 of the body 12 to the bile duct.

FIG. 4 illustrates an alternative embodiment of the prosthesis 10 showing a valve 40 extending proximally from the proximal portion 14 of the body 12. The valve 40 may be separate from the sleeve 22 so that the distal portion 36 of the sleeve 22 is distal to the valve 40. The distal portion 36 may be similar to the distal portions 36 in the embodiments described above. The valve 40 may be a one-way valve so that contents from the duodenum or the stomach do not travel through the lumen 18 of the body 12 to the bile duct. In some embodiments, the valve 40 may be a one-way valve positioned within the lumen 18 of the body 12 as shown in FIG. 5.

FIGS. 6 and 7 illustrate cross-sectional views through the body 12 of the prosthesis 10. FIG. 6 illustrates the body 12 having a substantially uniform circumference 38. The connected portion 24 is shown with the sleeve 22 connected to the body 12. The sleeve lumen 23 and the body lumen 18 are also shown. FIG. 7 illustrates an alternative embodiment showing the body 12 having one or more channels 52 involuted from the surface 26 of the body 12. The connected portions 24 are spaced apart from the channels 52 so that the sleeve lumen 23 is positioned between the body 12 and the sleeve 22. The channels 52 allow for fluid to continue flowing within the lumen 23 in the event that the sleeve 22 is pressed against the body 12 at an unconnected portion and fluid flow is inhibited.

FIGS. 8 and 9 illustrate embodiments of a prosthesis 100. The prosthesis 100 includes a body 112 having proximal portion 114, a distal portion 116 and a lumen 118 extending therethrough. As shown in FIGS. 8 and 9, the body 112 is provided as a non-expandable tubular stent. The body 112 is shown as a double pigtail stent but may also be provided having a single pigtail and/or skived portions on the proximal and/or distal portions 114, 116 to help hold the body 112 in position within the bodily site.

The prosthesis 100 further includes a sleeve 122 having a connected portion 124 to operably connect the sleeve 122 to the body 112 at at least one position along the body 112. The sleeve 122 is connected to the body 112 in such a way that fluid can pass through a sleeve lumen 123 between an outer surface 126 of the body 112 and an inner surface 128 of the sleeve 122. The connected portion 124 of the sleeve 122 is configured so that the connected portion 124 still allows fluid flow through the sleeve lumen 123 generally from a distal portion 132 of the sleeve 122 to a proximal portion 136 of the sleeve 122. The connected portion 124 may be similar to the connected portion 24 described above. As shown in FIGS. 8 and 9, the distal portion 132 of the sleeve 122 is unconnected to the body 112 of the prosthesis 100 and includes sufficient material to extend away from the body 112 as will be explained in more detail below. The distal portion 132 of the sleeve 122 may be collapsed against the body 112 for delivery of the prosthesis 100 to the bodily lumen and then the distal portion 132 may be extended away from the body 112 when the prosthesis 100 is in positioned within the bodily lumen.

The proximal portion 136 of the sleeve 122 may be sized and shaped to fit close to the body 112 as shown in FIG. 8 or to include sufficient material to extend away from the body 112 as shown in FIG. 9. In some embodiments, the proximal portion 136 of the sleeve 122 may be connected to the body 112 by a connected portion 124. In other embodiments, the proximal portion 136 of the sleeve 122 may be unconnected to the body 112 and sized closely fit to the body 112 or extended away from the body 112. In some embodiments, a diameter $d_1$ of the proximal portion 136 of the sleeve 122 may be smaller than a diameter $d_2$ of the distal portion 132 of the sleeve 122 as shown in FIG. 8. In some embodiments, the diameter $d_1$ of the proximal portion 36 may be the same or greater than the diameter $d_2$ of the distal portion 36 of the sleeve 22.

In some embodiments, the prosthesis 100 may include one or more channels 152 similar to the channels 52 described above.

FIG. 10 illustrates an embodiment of the prosthesis 10 wherein the body 12 includes an expanded proximal end portion 56 and an expanded distal end portion 58 that have larger diameters than a central portion 62 of the body 12. The expanded proximal and distal end portions 56, 58 may be used to help hold the prosthesis 10 in position within the body of the patient. The distal portion 32 of the sleeve 22 is shown expanded away from the distal end portion 58 of the body 12. Fluid may enter the sleeve lumen 23 or the body lumen 18 to drain fluid out of the duct as described in more detail below.

FIG. 11 illustrates the prosthesis 10 with the distal portion 16 of the body 12 positioned within the gall bladder or a hepatic duct 226 of the liver 227. The distal portion 32 of the sleeve 22 is positioned in the duct 226. The sleeve 22 is shown extended away from the distal portion 16 of the body 12 and positioned against a wall 225 of the duct 226. The distal portion 32 of the sleeve 22 is made of a flexible material so that the distal portion 32 can abut the wall 225 and generally conform to the shape of the wall 225 so that bile needing to drain from the duct 226 is captured by the distal portion 32 of the sleeve 22 and directed to the sleeve lumen 23. The bile can also drain through the lumen 18 of the body 12. As shown in FIG. 11, the body 12 and the sleeve 22 extend through the wall 225 of the duct 226, across the peritoneum 228, through a wall 229 of the gastrointestinal tract 230 and into the gastrointestinal tract 230. The proximal portion 14 of the body 12 is positioned within the gastrointestinal tract 230. The proximal portion 36 of the sleeve 22 also extends into the gastrointestinal tract 230 so that fluid entering the sleeve lumen 23 in the duct 226 is released in the gastrointestinal tract 230 and not the peritoneum 228. The sleeve 22 extends across the peritoneum 228 and retains the fluid within the lumen 23 of the sleeve 22 until the sleeve 22 opens within the gastrointestinal tract 230. The sleeve 22 may be connected to the body 12 at one or more connected portions 24. For example, the connected portion may be positioned near the wall 225 so that the distal portion 32 is free to expand against the wall 225 but once the sleeve 22 exits the wall 225, the connected portion 24 helps to maintain the sleeve 22 in close proximity to the body 12 so that the sleeve 22 does not gather together and block flow through the sleeve lumen 23. In some embodiments, the sleeve 22 may be sized and shaped to closely fit over the body 12 once the body 12 exits the wall 225 yet allows fluid flow through the sleeve lumen. In some embodiments, the sleeve 22 may be formed of stiffer material relative to the distal portion 32 once the sleeve 22 exits the wall 225. The length of the body 12 and the sleeve 22 will vary depending on the patient and will have sufficient length to extend between the duct 226 and the gastrointestinal tract 230.

The materials used to manufacture the components of the prosthetic devices described herein may be any materials known to one skilled in the art that are suitable for use in patients. By way of non-limiting example, the body may be formed from metals or polymers. Suitable exemplary metals include stainless steel and nitinol. In some embodiments, the body may be woven or provided in a zig-zag configuration. Sleeves of the prosthetic devices of the embodiments may be made from any suitable biocompatible material that is liquid impermeable and that does not degrade in the presence of fluids or gastric material that comes in contact therewith. By way of non-limiting example, the sleeve may be made from a medical grade expanded PTFE, polyurethane material, silicone, nylon, polyamides such as other urethanes, or other biocompatible materials that are flexible and acid resistant.

Figure 12:
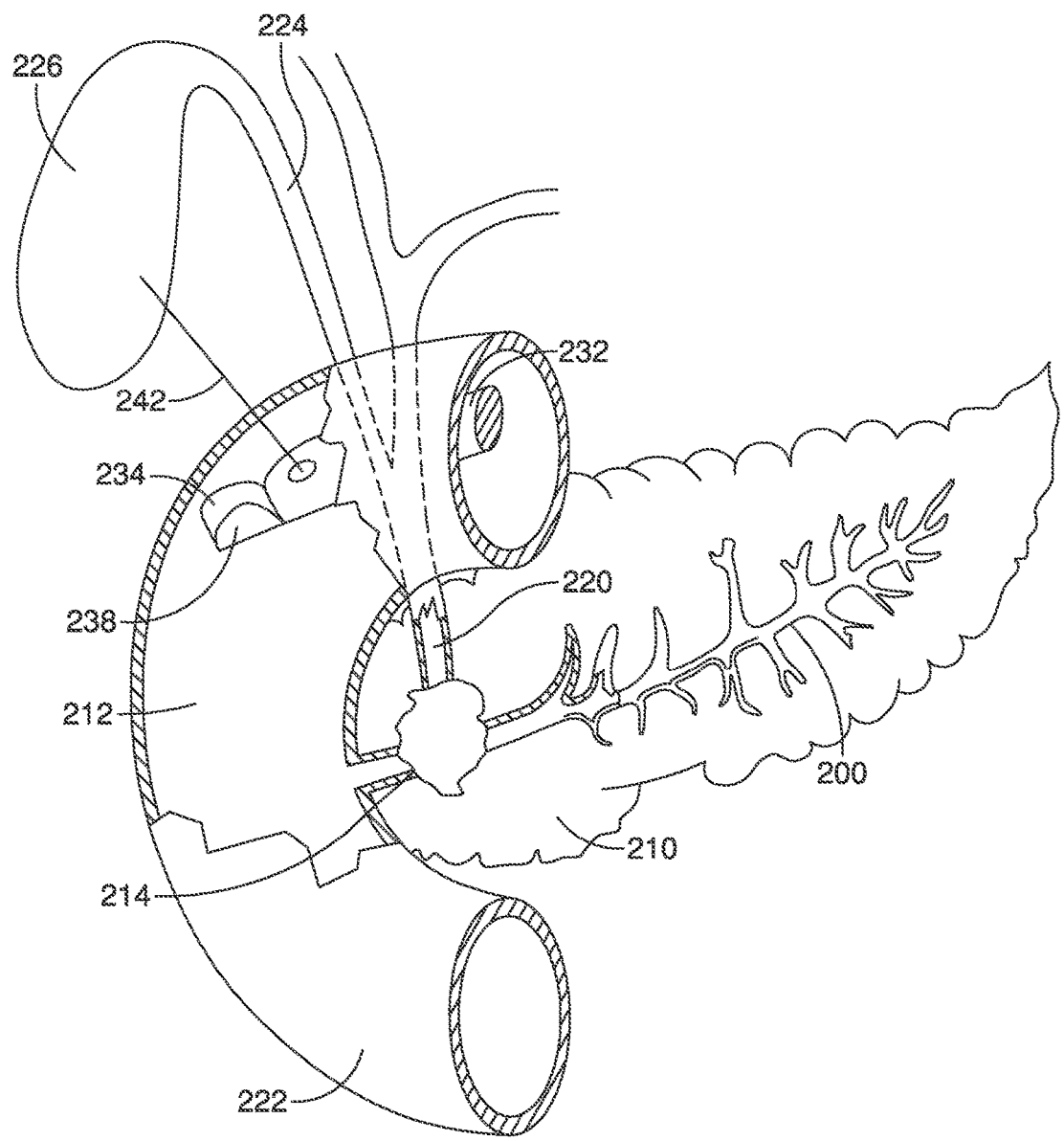
FIG. 12-14 illustrate delivery of an embodiment of a prosthetic device to the gall bladder and the gastrointestinal tract.
Figure 13:
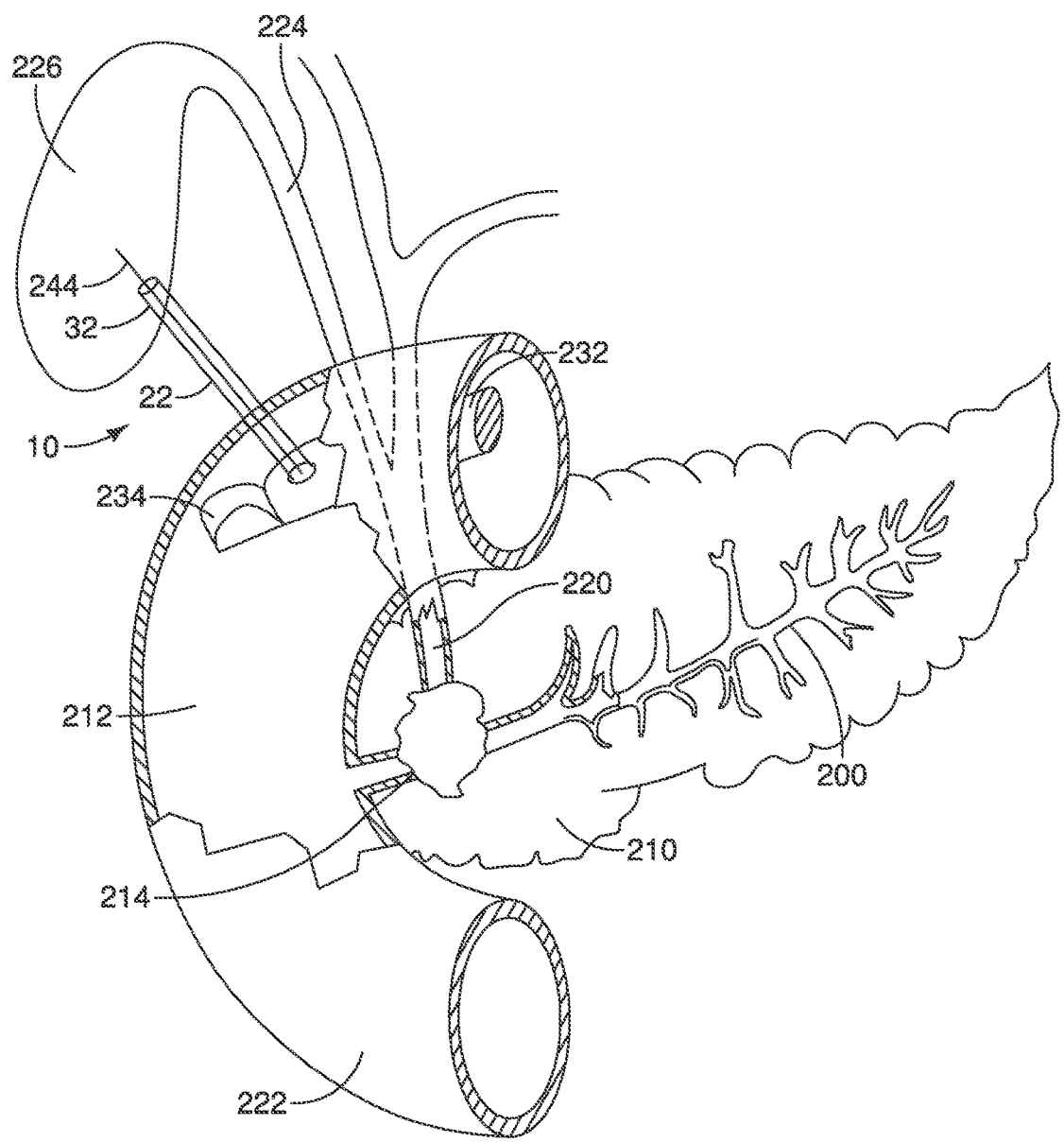
Figure 14:
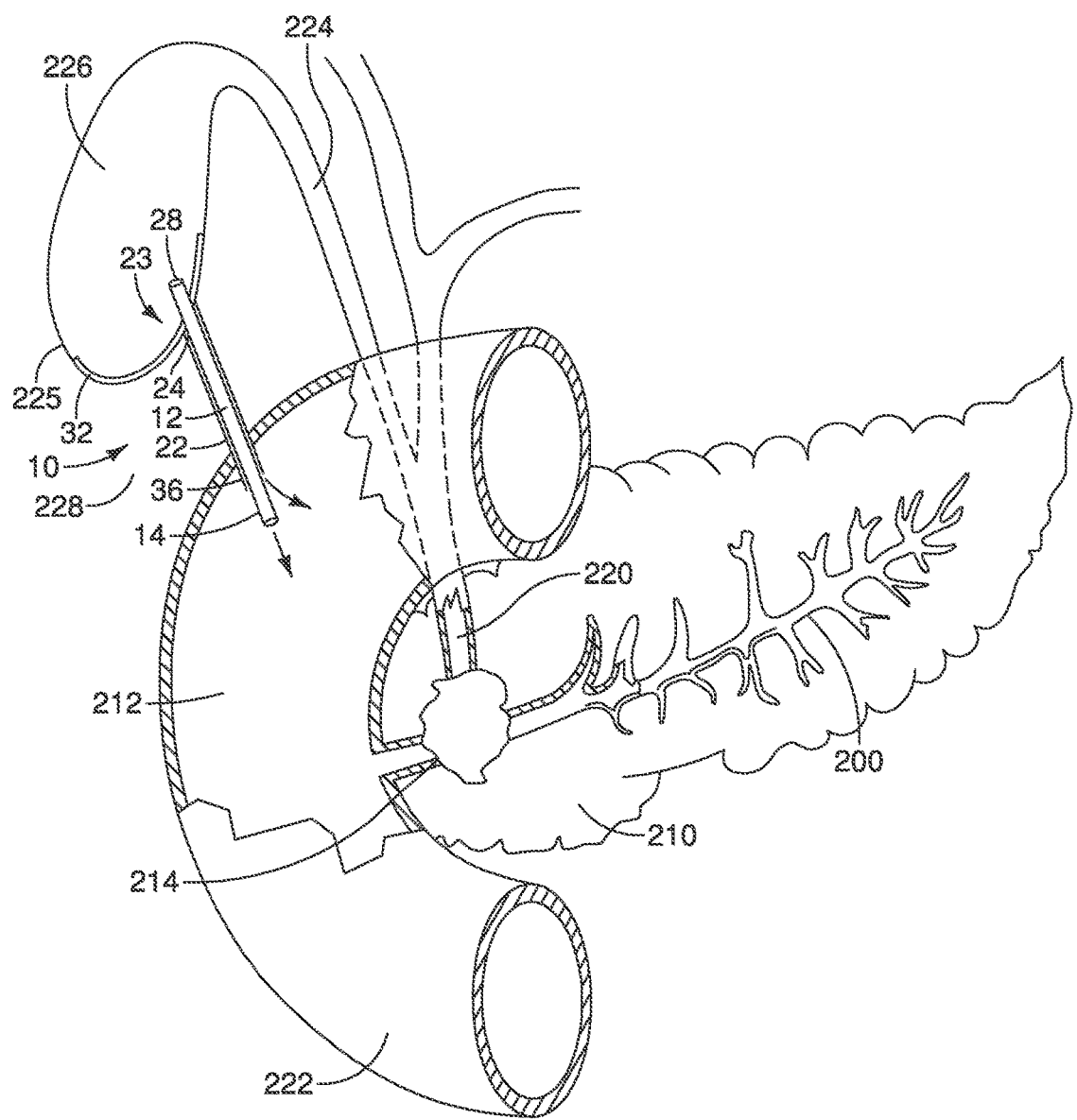

Delivery of the prosthesis will be explained with reference to the prosthesis 10 as an example and being positioned between the gall bladder and the duodenum. One skilled in the art will also understand that the prosthesis 10, 100 may be positioned between the hepatic duct and the stomach. FIGS. 12-14 illustrate delivery of the prosthesis 10. For reference, the pancreatic duct 200 of the pancreas 210 is shown having an obstruction 214 obstructing the common bile duct 220 and the pancreatic duct 200. The obstruction 214 prevents the placement of a biliary stent within the common bile duct 220 to allow the bile to drain.

Typically an endoscope or an endoscopic ultrasound (EUS) device that utilizes high frequency sound waves to create an image of living tissue or an echogenic surface, is positioned in the duodenum 212. An EUS device 232 is shown in FIG. 12 having an ultrasonic array of transducers 234 at the distal end 2388 of the endoscope 232. The transducers 234 may be connected to an imaging system (not shown) for viewing the image created by the ultrasonic transducers 234 to facilitate placement of the prosthesis 10. The transducers 234 generate an ultrasonic scanning plane to permit real-time monitoring of an insertion needle 242 having an echogenic surface. As shown in FIG. 12, the needle 242 is used to puncture the bile duct 226. Bile may be withdrawn through the needle and contrast may be injected to facilitate delivery of the prosthesis 10. A wire guide 244 may be inserted through the needle 242 and delivered to the bile duct 226. The prosthesis 10 is delivered from the duodenum 212 over the wire guide 244 into the gall bladder 226 as shown in FIG. 13. The sleeve 22 is delivered to the site positioned against the body 12. In some embodiments, an outer sheath may be placed over the sleeve 22 and body 12 for delivery of the prosthesis 10 to the site. In some embodiments, the distal portion 32 of the sleeve 22 may be temporarily secured to the distal portion 16 of the body 12, for example by a releasable suture or by a temporary glue that dissolves on contact with bodily fluids. Other methods for temporarily securing the distal portion 32 of the sleeve 22 to the body 12 are also possible.

FIG. 14 illustrates the prosthesis 10 positioned in the gall bladder 226 and extending across the peritoneum 228 into the duodenum 212. The distal portion 32 of the sleeve 22 is shown extended away from the distal portion 16 of the body 12 and positioned against the wall 225 of the gall bladder 226, generally conforming to the shape of the wall 225 so that bile needing to drain from the gall bladder 226 is captured by the distal portion 32 of the sleeve 22 and directed to the sleeve lumen 23. The bile can also drain through the lumen 18 of the body 12. The proximal portion 14 of the body 12 is positioned within the duodenum 212. The proximal portion 36 of the sleeve 22 also extends into the duodenum 212 so that fluid entering the sleeve lumen 23 in the gall bladder 226 is released in the duodenum 212 and not the peritoneum 228. The sleeve 22 extends across the peritoneum 228 and retains the fluid within the lumen 23 of the sleeve 22 until the sleeve 22 opens within the duodenum 212. In some embodiments, where the body 12 is an expandable stent, the body 12 may be expanded so that the diameter of the expanded stent is less than the diameter of the sleeve, at least at the mid portion of both the body and the sleeve.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A method of directing flow through a passageway formed between a first bodily lumen and a second bodily lumen, the method comprising:
   delivering a prosthesis comprising a body and a sleeve to a first bodily lumen and a second bodily lumen;
   positioning a distal portion of the sleeve and a distal portion of the body of the prosthesis within the first bodily lumen;
   positioning a proximal portion of the sleeve and a proximal portion of the body of the prosthesis within the second bodily lumen so that a portion of the body and a portion of the sleeve extend across the peritoneum between the first bodily lumen and the second bodily lumen, the sleeve being connected to the body at a connected portion;
   allowing the distal portion of the sleeve to extend away from the distal portion of the body and to conform to a wall of the first bodily lumen when the distal portion of the sleeve is positioned in the first bodily lumen;
   wherein the first bodily lumen and the second bodily lumen are fluidly connectable through a lumen of the sleeve so that flow can occur through the lumen of the sleeve from the first bodily lumen to the second bodily lumen, and wherein the sleeve is configured to allow fluid flow through the sleeve lumen between an outer surface of the body and an inner surface of the sleeve from the first bodily lumen to the second bodily lumen.

2. The method of claim 1, further comprising delivering the prosthesis through the second bodily lumen to the first bodily lumen.

3. The method of claim 1, comprising delivering the prosthesis using an endoscopic ultrasound device.

4. The method of claim 1, comprising delivering the prosthesis to the first bodily lumen with the sleeve positioned against the body.

5. The method of claim 1, comprising expanding the body comprising a self-expanding stent so that the expanded body has a diameter at a mid portion that is less than a diameter of the sleeve at a mid portion of the sleeve.

6. The method of claim 1, wherein the first bodily lumen comprises a gall bladder or a hepatic duct.

7. The method of claim 1, wherein the second bodily lumen comprises a duodenum or a stomach.

8. The method of claim 1, comprising inserting a needle into the first bodily lumen.

9. The method of claim 1, comprising inserting a wire guide into the first bodily lumen and delivering the prosthesis over the wire guide.

10. The method of claim 1, comprising delivering the prosthesis with a sheath over the sleeve and body and removing the sheath after delivery.

11. The method of claim 1, comprising delivering the prosthesis with the distal portion of the sleeve temporarily secured to the distal portion body.

12. The method of claim 1, wherein the sleeve comprises a fluid impermeable, flexible material so that the distal portion of the sleeve can conform to the wall of the first bodily lumen.

13. A method of directing flow through a passageway formed between a first bodily lumen and a second bodily lumen, the method comprising:
   delivering a prosthesis to a treatment site, the prosthesis comprising a body and a sleeve surrounding at least a portion of the body, the treatment site comprising a first bodily lumen and a second bodily lumen;
   positioning a distal portion of the sleeve and a distal portion of the body of the prosthesis within the first bodily lumen;
   positioning a proximal portion of the sleeve and a proximal portion of the body of the prosthesis within the second bodily lumen so that a portion of the body and a portion of the sleeve extend across the peritoneum between the first bodily lumen and the second bodily lumen;
   the distal portion of the sleeve being extendable away from the distal portion of the body and conformable to a wall of the first bodily lumen when the distal portion of the sleeve is positioned in the first bodily lumen, and wherein fluid is flowable between an outer surface of the body and an inner surface of the sleeve from the first bodily lumen to the second bodily lumen.

14. The method of claim 13, wherein the first bodily lumen and the second bodily lumen are fluidly connectable through a lumen of the sleeve so that flow can occur through the lumen of the sleeve from the first bodily lumen to the second bodily lumen to prevent fluid from flowing into the peritoneum.

15. The method of claim 13, comprising inserting a needle into the first bodily lumen and removing fluid from the first bodily lumen.

16. The method of claim 13, comprising delivering the prosthesis to the treatment site over a wire guide.

17. The method of claim 13, comprising positioning a retention device of the body in the first bodily lumen.

18. The method of claim 13, comprising restricting flow from the second bodily lumen toward the first bodily lumen.

* * * * *